(12) United States Patent
Weisbuch et al.

(10) Patent No.: US 7,306,766 B2
(45) Date of Patent: Dec. 11, 2007

(54) BIOCHIP TYPE DEVICE

(75) Inventors: Claude Weisbuch, Paris (FR); Henri Benisty, Palaiseau (FR)

(73) Assignees: Centre National de la Recherche Scientifique, Paris Cedex (FR); Ecole Polytechnique, Palaiseau Cedex (FR); Universite de Versailles Saint-Quentin en Yvelines, Versailles (FR)

( * ) Notice: Subject to any disclaimer, the term of this patent is extended or adjusted under 35 U.S.C. 154(b) by 318 days.

(21) Appl. No.: 10/849,141

(22) Filed: May 20, 2004

(65) Prior Publication Data

US 2004/0222480 A1    Nov. 11, 2004

Related U.S. Application Data

(63) Continuation of application No. PCT/FR02/03975, filed on Nov. 20, 2002.

(30) Foreign Application Priority Data

Nov. 22, 2001    (FR) .................................. 01 15140

(51) Int. Cl.
  *G01N 21/01*    (2006.01)
  *G01N 21/64*    (2006.01)
(52) U.S. Cl. .................................... 422/82.11; 436/172
(58) Field of Classification Search .............. 422/82.11
  See application file for complete search history.

(56) References Cited

U.S. PATENT DOCUMENTS

| | | | | |
|---|---|---|---|---|
| 5,275,924 A | * | 1/1994 | Devonald et al. | 430/495.1 |
| 5,444,807 A | * | 8/1995 | Liu | 385/125 |
| 6,130,780 A | * | 10/2000 | Joannopoulos et al. | 359/584 |
| 2002/0168640 A1 | * | 11/2002 | Li et al. | 435/6 |
| 2003/0031852 A1 | * | 2/2003 | Fink et al. | 428/292.1 |

FOREIGN PATENT DOCUMENTS

| | | |
|---|---|---|
| DE | 199 47 616 A1 | 5/2001 |
| FR | 2 793 560 A1 | 11/2000 |
| FR | 2 801 977 A1 | 6/2001 |

* cited by examiner

*Primary Examiner*—Jill Warden
*Assistant Examiner*—Paul S Hyun
(74) *Attorney, Agent, or Firm*—Birch, Stewart, Kolasch & Birch, LLP

(57) ABSTRACT

An improved biochip type device comprising a substrate (10) including an intermediate non-absorbent multilayer mirror (12) covered by a layer (14) of high refractive index material having chromophore elements (16) fixed thereon, the layer (14) further including feature (24) for extracting guided-mode light in order to recover the light emitted by the chromophore elements (16) into the layer (14) in response to light excitation, and direct the light to detection and measurement means.

17 Claims, 2 Drawing Sheets

BIOCHIP TYPE DEVICE

This application is a Continuation of copending PCT International Application No. PCT/FR02/03975 filed on Nov. 20, 2002, which designated the United States, and on which priority is claimed under 35 U.S.C. § 120, and 35 U.S.C. § 119(a) on patent application Ser. No(s). 01/15140 filed in France on Nov. 22, 2001, the entire contents of which are hereby incorporated by reference.

FIELD OF THE INVENTION

The invention relates to an improved biochip type device comprising a substrate, chromophore elements carried by the substrate, and means for picking up and concentrating the light emitted by the chromophore elements.

BACKGROUND OF THE INVENTION

Known techniques for detecting and quantifying chemical or biological molecules, and in particular nucleic acids, oligonucleotides, proteins, polypeptide sequences, or fragments of such compounds, make use of biochip type devices comprising substrates that are generally made of glass, silica, metal, or nylon, and having fixed thereon specific ligands ("probes") for the molecules that are to be analyzed. The molecules in a sample that is brought into the presence of these ligands couple with those ligands that match them. Radiation that is substantially monochromatic is used to excite chromophore elements that are associated with the molecules, and these elements respond by emitting luminescence or phosphorescence at some other wavelength, thus making it possible to identify the molecules that are coupled to the probes.

The chromophore elements are formed by the molecules themselves or else they are fixed or grafted to the molecules, or indeed they may be formed by the substrate itself on which the molecules become grafted, and they have light-emitting properties that depend on the presence and the nature of the grafted molecules.

In known devices, the probes are fixed in an array on the substrates and they are situated at known locations. The light signals emitted by the chromophore elements serve firstly to locate the probes to which molecules have coupled and to quantify the quantities of molecules that have coupled with the probes. Nevertheless, it is necessary to have a relatively large number ($10^4$) of molecules in the same category in order to obtain a usable light signal. In addition, the trend is to place ever increasing numbers of probes on substrates of very small dimensions, so that it becomes very difficult to locate with sufficient accuracy, and thus identify, the probes that are carrying the chromophore elements from which the detected light signals originate.

The conventional solutions usually implemented for solving this problem consist in increasing the signal level exciting the chromophore elements in order to increase the response light therefrom, or else in increasing the quantity of molecules that couple and/or the quantity of probes, however those means are not very satisfactory for reasons of poor energy efficiency and cost. Increasing the intensity of light excitation runs the risk of photodegradation of the molecules, and increasing the quantities of coupled molecules and probes requires an increase in the quantities of reagents used, which reagents are expensive.

Other known means use optical detection systems of very wide numerical aperture and/or immersed systems (in order to increase refractive index) but they are not very compatible with requirements for rapid scanning of arrays of probes on substrates.

Proposals have also been made to associate such biochip type devices with various means for picking up a larger fraction of the light emitted by the chromophore elements in response to light excitation, and for concentrating the picked-up light on detection and measurement means.

SUMMARY OF THE INVENTION

A particular object of the present invention is to increase measurement sensitivity by modifying the optical environment of each chromophore element, thus making it possible to pick up and concentrate on detection and measurement means a larger quantity of the light that is emitted by the chromophore elements.

To this end, the invention provides an improved biochip type device comprising a substrate, chromophore elements carried by the substrate, and means for picking up the light emitted by the chromophore elements in response to light excitation, the device being characterized in that the substrate includes a non-absorbent multilayer mirror covered by a layer of material having high refractive index which carries the chromophore elements and which includes means for extracting light in guided mode, these extraction means being arranged in the vicinity of the chromophore elements and being formed by a diffracting three-dimensional configuration or structuring of said layer.

In the device of the invention, each chromophore element carried by the layer of high index material radiates most of its light emission into said material at angles that are below the critical angle, so that the radiation is converted into guided mode within the layer of high index material. The diffracting three-dimensional configuration or structuring of said layer in the vicinity of each chromophore element enables the radiation in guided mode to be extracted and directed towards the detection and measurement means.

Thus, a major portion of the radiation emitted by each chromophore element can be picked up and used.

Advantageously, the diffracting three-dimensional configuration or structuring of the layer of high index material comprises planar photonic crystals or quasi-crystals formed by sets of holes made through said layer, with the dimensions and spacings of said holes being of the same order of magnitude as the wavelength of the radiation in guided mode.

According to another characteristic of the invention, the layer of high refractive index material, the above-mentioned non-absorbent multilayer mirror, and the interface surface between the high refractive index material and the surrounding medium (gas or liquid) together constitute a resonant planar microcavity.

This resonant microcavity placed under the chromophore elements is of a thickness that is selected to deliver a maximum amount of the light emitted by the chromophore elements towards the detection and measurement means. The effect due to this resonant microcavity combines with the effect due to extracting guided-mode light from the layer of high index material, thereby providing maximum effectiveness in picking up and concentrating the light emitted by each chromophore element.

According to yet another characteristic of the invention, said layer of high refractive index material constitutes a planar waveguide into which the light for exciting the chromophore elements is coupled, either via an edge of said layer, or by means of at least one coupling grating formed on the surface of said layer.

Exciting chromophore elements by light guided in said layer is advantageous, but said excitation light must not itself be extracted from said layer by the above-mentioned means for extracting the light emitted by the chromophore elements.

For this purpose, it is advantageous for the chromophore elements to be arranged on said layer in at least one row or strip, and preferably in a plurality of parallel rows or strips to form an array, and for the means that extract the light emitted by the chromophore elements to be arranged in an array along each strip of chromophore elements, on either side of the elements.

The chromophore elements of each strip are then excited by a collimated light beam of small divergence traveling along the strip direction and of a width that is slightly less than or equal to the corresponding dimension of a chromophore element.

Each strip of chromophore elements receives a different excitation light beam, which can propagate over a distance of several millimeters while conserving relatively narrow width and which does not reach the above-mentioned extraction means which are on the sides of the strip of chromophore elements.

In general, the device of the invention makes it possible to obtain a signal/noise ratio that is higher than in the prior art and to reject effectively the light for exciting the chromophore elements. This makes it possible to perform measurements in parallel by imaging the device, and also makes it possible to extend the operation of the device to a plurality of wavelengths.

Typically, the efficiency with which the light emitted by the chromophore elements is picked up and the total measurement sensitivity are multiplied by a coefficient of at least five compared with known devices in the prior art.

The invention has multiple applications, for example in diagnosing genetic diseases (cancer, diabetes, obesity, cardiovascular disease, etc.), for developing medicines (that are genetically expressed), for food and environmental testing (bacteriological, viral, and transgenic inspection), and fundamental research in biology (genome sequencing, etc.).

The invention will be better understood and other characteristics, details, and advantages thereof will appear more clearly on reading the following description, made by way of example and with reference to the accompanying drawings, in which:

DETAILED DESCRIPTION OF THE INVENTION

Figure 1:
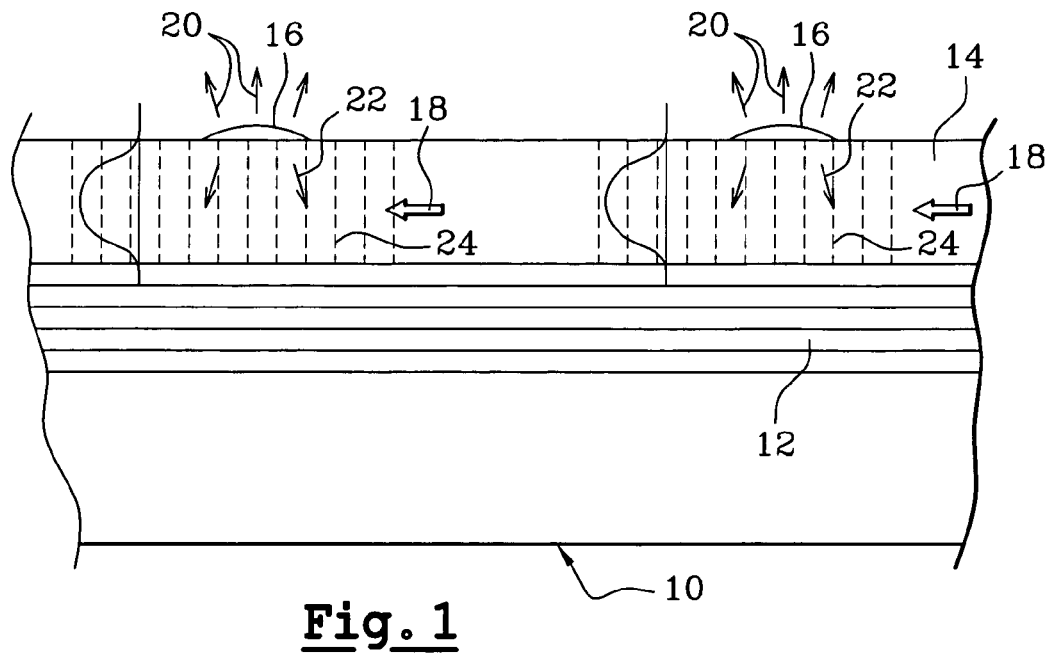
FIGS. 1 and 2 are fragmentary large-scale views respectively in section and as seen from above showing a device of the invention.
Figure 2:
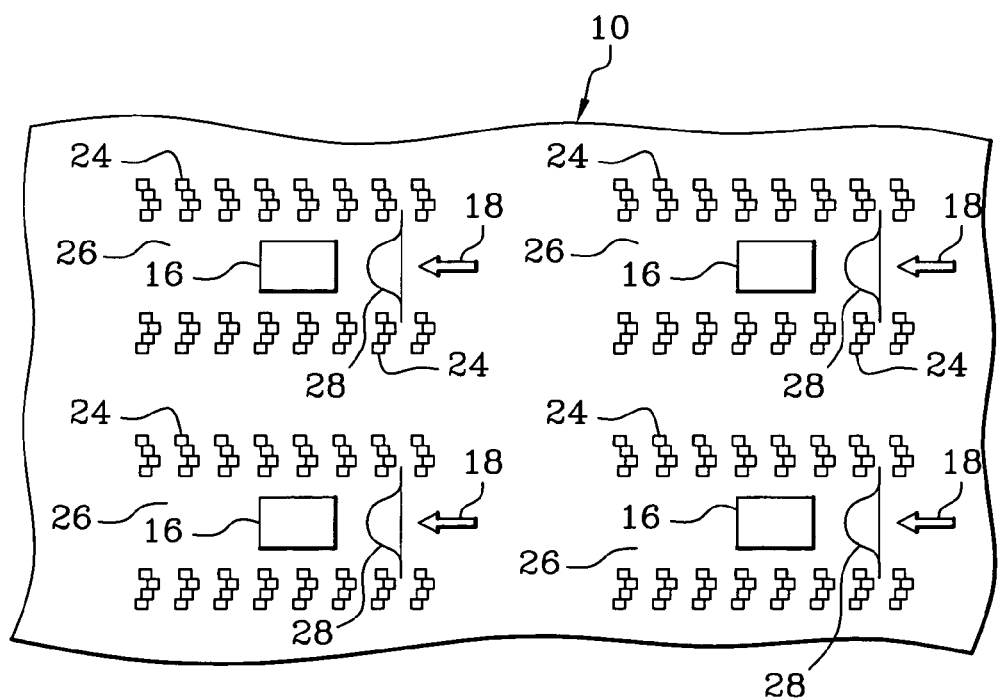

In the embodiment of FIGS. 1 and 2, reference 10 designates a substrate of any suitable material, e.g. glass, silica, metal, semiconductor material, or oxide, the substrate including an intermediate non-absorbent multilayer mirror 12 made up of a plurality of dielectric or metallic layers covered in a layer 14 of material having a relatively high refractive index, i.e. in this case a material whose refractive index is greater than or equal to 1.6. For example, the material may be $TiO_2$ which has a refractive index equal to 2.4.

Chromophore elements 16 are fixed to the top face of the layer 14.

As mentioned above, these chromophore elements may be formed by probes fixed on the top face of the layer 14, or by molecules for analysis that become coupled with the probes that match them.

These probes constitute an array on the surface of the layer 14 and they are located in known positions.

Typically, the chromophore elements 16 are on squares of a side lying in the range a few tens of micrometers ($\mu m$) to about 1 millimeter (mm). They form a layer that is optically very thin on the surface of the layer 14, and this very thin layer gives rise to little diffusion of guided light.

The chromophore elements 16 are excited by means of a substantially monochromatic light beam of predetermined wavelength, which is coupled into the layer 14 either via an edge of said layer, or else by means of a coupling grating formed on the surface of the layer 14 in a manner that is known to the person skilled in the art, e.g. by means of a thin layer of photosensitive resin with small thickness modulation.

The excitation beam is shown diagrammatically at 18 in FIGS. 1 and 2.

The chromophore elements 16 excited by the beam 18 respond by emitting luminescence or fluorescence, a fraction 20 of which is radiated upwards in a direction substantially perpendicular to the layer 14 and can be picked up directly by optical detection and measuring means, while another fraction 22 is radiated in guided mode in the layer 14 and is extracted therefrom by means of an extraction grating 24 formed in the layer 14 in the vicinity of the chromophore elements 16, and on either side thereof.

More precisely, the chromophore elements 16 are arranged on the surface of the layer 14 in parallel rows or strips 26 that are substantially equidistant, each being illuminated by a collimated excitation light beam 18, having narrow width of the same order of magnitude as the corresponding dimension of a chromophore element 16. These low-divergence beams 18, e.g. having divergence of less than 20 milliradians (mrad) conserve a beam width lying in the range approximately 50 $\mu m$ to 100 $\mu m$ over a length of several millimeters, for a visible light laser beam, with the beams being, for example, of the Gaussian type in the plane of FIG. 2, as shown at 28, with an antinode in the middle of each strip 26.

Each excitation beam 18 may be produced by a separate laser diode and it is collimated by means of cylindrical lenses.

The extraction gratings 24 are on the sides of the strips 26, on either side of the chromophore elements 16 relative to the direction of the excitation light beam 18 and they extend over sufficient length parallel to the direction of the excitation beam 18 to intercept the major portion (about 80%) of the light emitted in guided mode by each chromophore element 16 into the layer 14 of material having a high refractive index. For example, the length of the gratings 24 is about three times the corresponding dimension of a chromophore element.

It is known that a dipole placed in the immediate vicinity of an interface between two media of indices that are very different, as is the case for the above-mentioned layer 14 and the layer covering it (gas or liquid), has a tendency to radiate the major portion of its light emission into the medium having the higher index, at angles which are smaller than the critical angle, so that said emission is converted into a guided mode in the planar structure formed by the high index material.

In the present case, the chromophore elements 16 placed at the interface between the layer 14 and the layer of fluid (gas or liquid) covering it tend to radiate the major portion of their luminescence or fluorescence into the layer 14, and this radiation is converted into guided mode in said layer.

Figure 3:
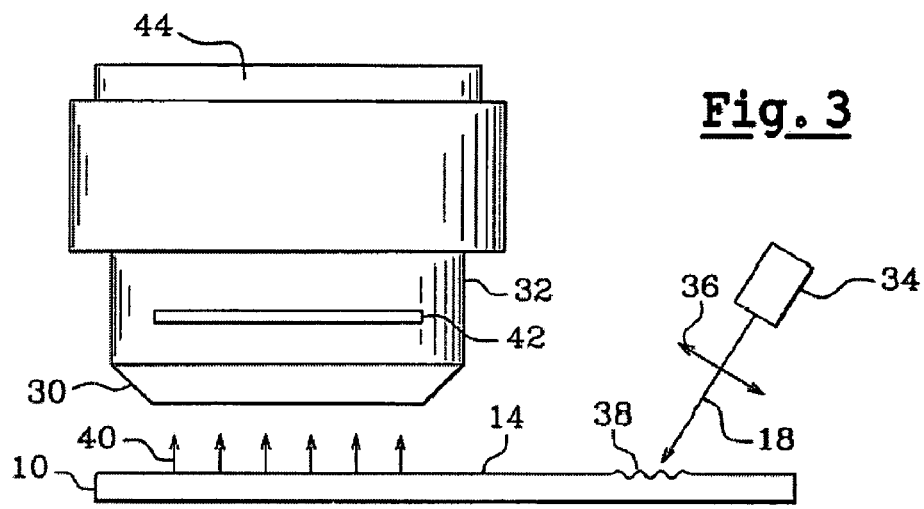
FIG. 3 is a diagram of detection and measurement means associated with a device of the invention.

The extraction gratings 24 formed on either side of the chromophore elements 16 on the sides of the strips 26 serve to extract said guided-mode light and to direct it substantially perpendicularly to the layer 14 towards optical detection and measurement means situated above said layer, as explained below with reference to FIG. 3.

The extraction means 24 are planar phonotonic crystals or quasi-crystals made up of sets of holes, e.g. periodic sets, formed through the layer 14 and constituting a diffractive three-dimensional configuration or structuring, with the dimensions and spacings of the holes being of the same order as the wavelength of the light in guided mode in the layer 14, the thickness of this layer being about 1 µm or less, for example.

The photonic crystals or quasi-crystals 24 are preferably tiled as substantially touching polygons, and connected to adjacent polygons via each of their sides, the tiling possibly presenting a wide variety of shapes, the unit pattern or "motif" of the grating lattice possibly being, for example, an equilateral triangle, a lozenge, a square, or a hexagon. In this tiling, the holes in the layer 14 (or in equivalent manner the columns of materials that are separated by the holes) are to be found on the sides of the polygons of the tiling or at the vertices of said polygons.

The tiling may have one or more gaps so as to form a structure of amorphous type. It constitutes a diffracting structure which enables the light guided by the layer 14 to be extracted for incidence that is quasi-omnidirectional in the plane of said layer.

The holes forming this structure may be made by any appropriate means, for example by a planar lithographic method derived from microelectronics.

Typically, the extraction gratings 24 formed on either side of the chromophore elements 16 are of length equal, for example, to three times the length of the chromophore element, and are of width equal to a few µm, thus making it possible to have a distance between excited strips 26 that is small, for example about 20 µm to 50 µm only, and to obtain a device of the invention that is very compact.

In addition, the layer 14 of material having relatively high index constitutes a resonant planar microcavity defined by the above-mentioned multilayer mirror 12 and by the interface surface between the layer 14 and the surrounding fluid medium (gas or liquid). The thickness of this microcavity is selected to send a maximum amount of the light emitted by the chromophore element 16 into an objective lens 30 of detection and measurement means 32 shown diagrammatically in FIG. 3.

In this figure, reference 34 designates means, such as a laser diode for example, for generating an excitation light beam 18 that is collimated, for example by means of a cylindrical lens 36 and that is coupled into the layer 14 by a grating 38 of small modulation thickness.

References 40 designate both the light sent directly by the planar microcavity towards the lens 30 and the light extracted from the layer 14 by the extraction gratings 24.

The detection and measurement means 32 include rejection filters 42 that allow the light at the emission wavelength of the chromophore elements 16 to pass towards an array 44 of photodetectors of the charge-coupled device (CCD) type, or the like.

The combination of the resonant planar microcavity formed by the layer 14 with the substantially omnidirectional extraction gratings 24 makes it possible to recover and direct to the lens 30 the major fraction of the light emitted by the chromophore elements 14 in response to excitation by the light beams 18. The improved sensitivity gain of the detection and measurement means has, as a direct consequence, improvements in several operating parameters, such as:

speed of analysis: this parameter is often limited by the power of the light signal as collected, which in this case is greatly increased;

the minimum quantity of substance required for analysis: this parameter can be made smaller in the invention in correspondence with the gain obtained in optical sensitivity;

the volume/weight ratio of devices of the invention: this parameter is directly linked with the preceding parameter, making it possible to provide equipment that is portable, with all of the operational advantages inherent thereto;

measurement accuracy: accuracy increases when a large number of probes are carried on the same substrate, since that requires great accuracy in geometrically locating the detected light signal;

primary emission power requirement: this parameter is crucial for biological compounds that are particularly fragile and that might be partially destroyed or spoilt by light power exceeding their admissible tolerance thresholds; and the size of the accessible analysis spectrum: the number of different probes on the same substrate can be very greatly increased by the improvement in measurement sensitivity.

In addition, the device of the invention is usable with excitation light beams of different wavelengths for detecting and measuring the light responses of chromophore elements at different wavelengths (using chromophores of "different colors").

Under such circumstances, the resonant microcavity defined by the mirror 12 and by the interface surface between the layer 14 and the surrounding medium must be tuned to a plurality of wavelengths simultaneously, these wavelengths being the emission maxima of the chromophore elements in response to being excited by light at different wavelengths. To do this, the thickness of the cavity needs to be significantly greater than that mentioned above. For example, if the wavelengths of the emission maxima of the chromophore elements 16 are 550 nanometers (nm) and 680 nm, then resonance can be obtained at those two wavelengths by a cavity of thickness (thickness of the layer 14) lying in the range approximately 1 µm to 2 µm, depending on refractive index. In addition, it is also possible to modify the penetration depth of the multilayer mirror 12 by means that are well known to the person skilled in the art.

Figure 4:
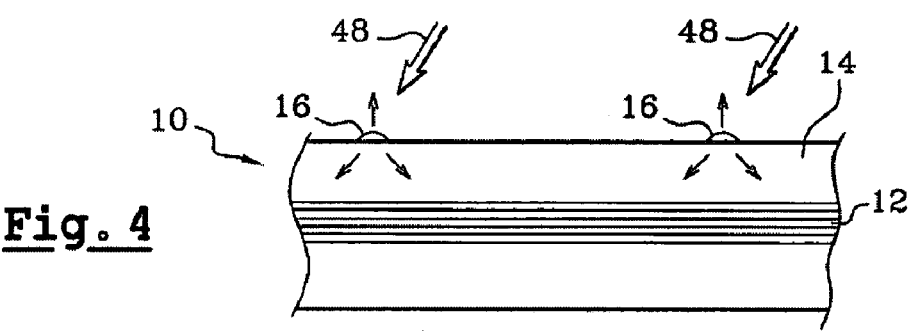
FIGS. 4 and 5 are views similar to FIGS. 1 and 2 for a variant embodiment.
Figure 5:
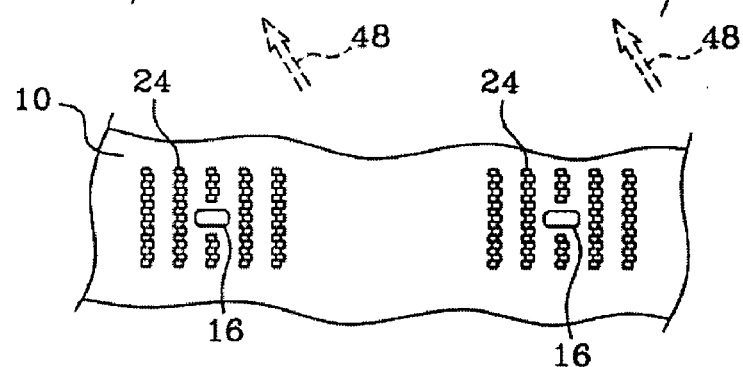

In the variant embodiment shown diagrammatically in FIGS. 4 and 5, the chromophore elements 16 carried by the layer 14 of the substrate 10 are excited by monochromatic light beams 48 external to the substrate 10 and directed either towards the face of the substrate carrying the chromophore elements, as shown in continuous lines, or else towards the opposite face of the substrate as shown in dashed lines.

In this variant, since the light excitation is not guided in the high index layer 14, the extraction means 24 can surround the chromophore elements 16 almost completely, as shown in FIG. 5.

The extraction means 24 may be defined by a wide variety of tilings constituted by convex polygons that are substantially touching, each sharing each of its sides with a single neighbor, these sides being of substantially the same size.

Figure 6:
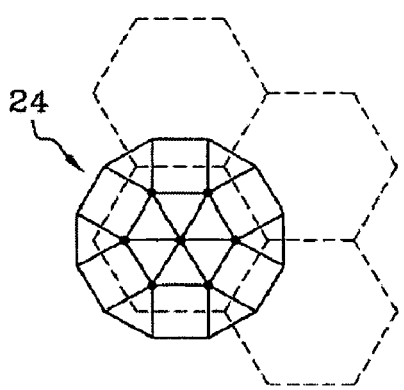
FIG. 6 is a fragmentary view on a larger scale of an example of a photonic crystal or quasi-crystal tiling.

In order to increase extraction efficiency, it is preferable to use complex tilings, presenting symmetry levels greater than 6. They may be constituted, for example, by Archimedian tilings formed using equilateral triangles and squares all having sides of the same size, as shown in FIG. 6, the holes or columns in the photonic crystal or quasi-crystal being located, for example, at the vertices of the polygons.

These tilings may be formed of substantially equal or comparable portions of squares and of equilateral triangles, or of first and second lozenges having different vertex angles. They may be constructed by periodization of a unit pattern comprising a selected number of equilateral triangles and squares, or by Stampfli inflation of such a pattern, or indeed by a random distribution of selected proportions of squares and equilateral triangles, or of first and second lozenges.

Furthermore, the photonic crystal or quasi-crystal can be made in the form of a tiling as described above, having at least one of the diffracting elements thereof omitted, so as to form a structure of amorphous type.

The invention claimed is:

1. An improved biochip type device comprising a substrate, chromophore elements carried by the substrate, and means for picking up light emitted by the chromophore elements in response to light excitation, wherein the substrate includes a non-absorbent multilayer mirror covered by a layer of material having high refractive index to which the chromophore elements are fixed and which includes means for extracting light in guided mode, these extraction means being arranged under the chromophore elements and having a diffracting three-dimensional configuration, the extraction means being constituted by sets of holes formed through said layer, the sets of holes constituting planar photonic crystals or quasi-crystals.

2. A device according to claim 1, wherein the sets of holes are periodic.

3. A device according to claim 1, wherein the dimensions and the spacings of the holes of the said layer are of the same order as the wavelength of the light in guided mode.

4. A device according to claim 1, wherein said layer of high refractive index material, the multilayer mirror and an interface surface between said high refractive index material and a surrounding medium together constitute a resonant planar microcavity.

5. A device according to claim 1, wherein said layer of high refractive index material constitutes a planar waveguide into which the excitation light for the chromophore elements is coupled, either through an edge of said layer, or by means of at least one coupling grating formed on the surface of said layer.

6. A device according to claim 1, wherein the chromophore elements are adapted to be excited by external light beams directed against one of two opposed faces of the substrate, said faces comprising the face carrying the chromophore elements and the face of the substrate opposite from that carrying the chromophore elements.

7. A device according to claim 1, wherein the chromophore elements are arranged on said layer in a plurality of parallel.

8. A device according to claim 1, wherein the chromophore elements are of dimensions lower than 1 mm, approximately.

9. A device according to claim 7, wherein the chromophore elements of a strip are excited by a low-divergence collimated light beam of width less than or equal to the corresponding dimension of the chromophore elements.

10. A device according to claim 9, wherein the excitation light beams of the various strips of chromophore elements are produced by different light sources.

11. A device according to claim 7, wherein the means for extracting guided-mode light are arranged in gratings along each strip of chromophore elements, on either side of said elements.

12. A device according to claim 6, wherein the means for extracting guided-mode light surrounds each chromophore element.

13. A device according to claim 11, wherein the extraction means form tilings of substantially touching polygons extending along each chromophore element over a distance equal to several times the corresponding dimension of the chromophore element.

14. A device according to claim 11, wherein the extraction means are of a transverse dimension that is small relative to the corresponding dimension of a chromophore element.

15. A device according to claim 1, wherein the thickness of said layer of high index material is less than or equal to 1 µm approximately.

16. A device according to claim 4, wherein the thickness of said layer of high index material is determined so that said resonant cavity is tuned to at least two different wavelengths corresponding to light emission maxima of the chromophore elements.

17. A device according to claim 1, wherein the refractive index of said layer is greater than or equal to about 1.6.

* * * * *